United States Patent [19]
Sox

[11] Patent Number: 6,100,245
[45] Date of Patent: Aug. 8, 2000

[54] USE OF SIMETHICONE TO TREAT ULCERATIVE COLITIS

[75] Inventor: Thomas Sox, Ambler, Pa.

[73] Assignee: McNeil-PPC, Inc., Skillman, N.J.

[21] Appl. No.: 09/390,812

[22] Filed: Sep. 7, 1999

[51] Int. Cl.$^7$ ........................ A61K 31/695; A61K 31/655
[52] U.S. Cl. ............................ 514/63; 514/820; 514/156
[58] Field of Search ............................... 424/724, 78.01; 514/156, 63, 820

[56] References Cited

U.S. PATENT DOCUMENTS

| | | | |
|---|---|---|---|
| 4,195,084 | 3/1980 | Ong ........................................ | 424/238 |
| 5,120,533 | 6/1992 | Schmidt et al. ..................... | 424/78.08 |
| 5,277,902 | 1/1994 | Schmidt et al. ..................... | 424/78.37 |
| 5,393,745 | 2/1995 | Schmidt et al. ......................... | 514/63 |
| 5,418,220 | 5/1995 | Schmidt et al. ......................... | 514/63 |
| 5,424,064 | 6/1995 | Schmidt et al. ..................... | 424/78.37 |
| 5,525,605 | 6/1996 | Omura ................................... | 514/258 |
| 5,599,577 | 2/1997 | Stevens et al. ....................... | 427/2.14 |
| 5,679,376 | 10/1997 | Stevens et al. ....................... | 424/472 |
| 5,716,641 | 2/1998 | Stevens et al. ....................... | 424/472 |
| 5,834,004 | 11/1998 | Upmeyer et al. .................... | 424/423 |
| 5,843,479 | 12/1998 | Kelm et al. .......................... | 424/479 |

FOREIGN PATENT DOCUMENTS

| | | | |
|---|---|---|---|
| 57566 | 11/1967 | France . | |
| WO 95/25545 | 9/1995 | WIPO ........................... | A61K 47/34 |

OTHER PUBLICATIONS

Efficacy and tolerability of polyethylene glycol–electrolyte lavage solution with and without simethicone in the preparation of patients with inflammatory bowel dises for colonoscopy. Lazzaroni, M. et al. Alimentary pharmacology & Therapeutics, (1993) vol. 7, No. 6, pp. 655–659.

Igor Laufer, "A Simple Method for Routine Double–Contrast Study of the Upper Gastrointestinal Tract" (Radiology, vol. 117, No. 3, 1975) 513–518.

Kazuo K. Kimura, Joseph F. Treon, and Frederic R. Benson, "Therapeutic Use of Methylopolysiloxane" (Current Therapetuic Research, vol. 6, No. 3, 1964) 202–215.

D.M. Preston and J.E. Lennard–Jones, "Pelvic Motility and Response to Intraluminal Bisacodyl in Slow–Transit Constipation" (Digestive Diseases and Sciences, vol. 30, No. 4, 1985) 289–294.

Von W. Roth and Unter Mitarbeit von K. Beschke, Pharmakokinetik und Laxierende Wirkung von Bisacodyl nach Gabe verschiedener Zubereitungsoformen, (Araneim–Forsch/Drug Res. 38(I), Nr. 4, 1988) 570–574.

Stephan R. Targan, "The Search for Pathogenic Antigens in Ulcerative Colitis" (Gastroenterology, vol. 114, No. 5, 1998) 1099–1100.

*Primary Examiner*—Theodore J. Criares
*Assistant Examiner*—Jennifer Kim

[57] ABSTRACT

The present invention provides compositions and methods for treating ulcerative colitis by providing an effective amount of simethicone and in a preferred embodiment in combination with sulfasalazine.

13 Claims, No Drawings

USE OF SIMETHICONE TO TREAT ULCERATIVE COLITIS

FIELD OF THE INVENTION

The present invention relates to a method of treating ulcerative colitis via the administration of an effective amount of simethicone.

BACKGROUND OF THE INVENTION

Colitis is understood to be the inflammation of the colon. A chronic type of colitis is ulcerative colitis of an unknown etiology characterized by ulceration of the colon and rectum, with rectal bleeding, mucosal crypt abscesses, inflammatory pseudopolyps, abdominal pain and diarrhea. Ulcerative colitis frequently causes anemia, hypoproteinemia, and electrolyte imbalance and is less frequently complicated by peritonitis, toxic megacolon or carcinoma of the colon.

Ulcerative colitis is frequently treated with various drugs including sulfasalazine. While these treatments are somewhat effective in treating the symptoms, there is a continuing need for additional treatments for this disease, perhaps a treatment which could be used to enhance the efficacy of the existing treatments.

SUMMARY OF THE INVENTION

The present invention provides a method of treating ulcerative colitis in a patient through the administration of an effective amount of simethicone. In a preferred embodiment, an effective amount of a second active ingredient for treating ulcerative colitis, such as sulfasalazine is employed.

DETAILED DESCRIPTION OF THE INVENTION

Simethicone is a well known pharmaceutical material which is a mixture of linear siloxane polymers containing repeating units of the formula $\{-SiO(CH_3)_2-\}_n$ stabilized with trimethylsiloxy endblocking units of the formula $[(CH_3)_3SiO-]$, and silicon dioxide. The level of simethicone in the present invention is sufficient to provide treatment of ulcerative colitis. As used herein, treatment of ulcerative colitis is understood to be a reduction in the amount of bleeding in the patient. The present invention contemplates the treatment of a human or animal, through any suitable dosage forms. Suitable forms includes solids, such as tablets or powders, liquids including suspensions, dispersions and solutions and the like. The preferred route of administration of the simethicone is oral administration, although other techniques known in the art may also be employed.

The effective level of simethicone is generally from about 0.5 mg/kg of body weight per day to about 40 mg/kg of body weight per day, preferably from about 1 mg/kg of body weight per day to about 20 mg/kg of body weight per day, and most preferably from about 5 mg/kg of body weight per day to about 10 mg/kg of body weight per day.

The present invention can incorporate other known pharmaceutically active ingredients for the treatment of colitis. Specific groups of ingredients which may be used to treat ulcerative colitis include immunosuppressive, antimicrobial, antidiarrheal, and anticholinergic agents. Of the immunosuppressive agents, sulfasalazine is preferred.

Commonly known pharmaceutically acceptable additives for orally-administered drugs such as sweeteners, flavoring agents, dispersants, buffering agents and the like may be included in amounts that do not adversely affect the novel properties of the formulation described and claimed herein. Suitable dispersants include methylcellulose, hydroxymethyl-cellulose, hydroxypropylmethylcellulose, hydroxyethyl-cellulose and the like. Suitable sweeteners include sugar, sorbitol, saccharin, mannitol, glucose, aspartame and the like. Flavoring agents include peppermint, spearmint, cinnamon, vanilla and the like. A more complete listing of appropriate additives can be found in numerous publications including Remington's Encyclopedia.

The present invention is surprising and unexpected in that PCT EP95/00973 previously disclosed that polydimethylsiloxane, also known as dimethicone, is effective in association or affinity to the surface structure of the GI tract. The PCT patent application continues that due to the increased adhesion properties of dimethicone, the residence time of an active ingredient in a region of the GI tract can be substantially prolonged if dimethicone is used as a transport or carrier system. This is contrary to the disclosed invention in which simethicone, which as noted above is a combination of polydimethylsiloxane and silicon dioxide, is effective in being transported to the distal regions of gastrointestinal tract.

The following examples are provided to further illustrate the claimed invention, but not limit the invention to the examples provided below.

EXAMPLE 1

This investigation used an experimental system in which ulcerative colitis is induced in mice by incorporation of dextran sulfate in the drinking water. For further detail, see Okayasu, I., et al., Gastroenterology 98:694–702 (1990), and Murthy, S., et al., Digestive Diseases and Science 38:1722–34 (1993). This experimental system has been used previously for the evaluation of the efficacy of pharmaceuticals compounds against ulcerative colitis. For example, see Murthy et al., supra, and U.S. Pat. No. 5,869,048, hereby incorporated by reference.

Female mice weighing between 26 and 33 grams were segregated into five groups of fifteen mice per group. At the beginning of the study the mice were allowed water ad libitum. After the initial acclimatization period, four groups of mice were switched from water to 5% weight dextran sulfate solution (30,000 to 40,000 molecular weight, ICN Biochemicals, Inc., Cosa Mesa, Calif.) in order to induce ulcerative colitis. The fifth group did not receive dextran sulfate, but remained on water. The four groups of mice received dextran sulfate solution for five days and then returned to water for the remainder of the study.

The four groups of mice were then treated as follows: a control was feed laboratory water; a second group received sulfasalazine (400 mg/kg); a third group received simethicone as a 30 percent emulsion (10 mg/kg); and the fourth group received sulfasalazine and simethicone (400 mg/kg and 10 mg/kg). Dosing was performed by a single oral gavage on each day of the treatment period, and the dose volume was 0.3 ml per mouse. Sulfasalazine was purchased from Sigma Chemical Company (St. Louis, Mo.) and simethicone, in the form of a 30% emulsion, was obtained from Dow-Corning (Midland, Mich.). The dosing preparations were made fresh each day, and the dosing preparations were used within one hour after preparation. Simethicone containing preparations were stirred continuously to ensure homogeneity.

As expected, some mice died due to consequences of severe colitis before the conclusion of the experiment. On the eleventh day, including five days of treatment with dextran sulfate followed by five days treatment with the test agent, measurement of colitis severity were obtained by standard methods as follows.

Mice were examined for signs of diarrhea, stool specimens were examined and tested for gross and occult blood (Hemoccult Strips® SmithKline Diagnostics, San Jose, Calif.) and the mice were weighed and sacrificed. For each mouse that survived the entire 10 day treatment, the abdomen was opened, the colon removed and colon length from cecum to rectum were measured. These colon measurements were performed as an indication of the inflammatory changes occurring in the colon during colitis and the severity of colitis induced in the mouse. For each mouse, weight loss, weight loss score, stool consistency score, stool blood score and colon length (centimeters) were recorded. The disease activity index (DAI) was calculated by addition of the weight loss, stool consistency and stool blood scores. The criteria for each are set forth below:

|  | Condition | Score |
|---|---|---|
| Weight Loss | | |
| | loss of less than a gram | 0 |
| | loss of 1.0 to 5.0 grams | 1 |
| | loss of 5.1 to 10.0 grams | 2 |
| | loss of 10.1 to 15.0 grams | 3 |
| | loss of more than 15 grams | 4 |
| Stool Consistency | | |
| | normal stool | 0 |
| | loose stool | 1 |
| | diarrhea | 2 |
| Stool blood | | |
| | normal stool | 0 |
| | occult blood present | 1 |
| | gross blood present | 2 |

Among the mice treated with dextran sulfate and which received no further treatment, the mortality was 67% (10 of 15). The mice treated with sulfasalazine, simethicone and the combination of sulfasalazine and simethicone had a much lower mortality rate, 40, 47 and 40 percent respectively.

Sulfasalazine produced improvement in all measures of colitis severity. Compared to respective control values, weight loss was less (10.4+/−3.6 percent), scores for diarrhea, bloody stool and DAI were less (scores 0.8+/−0.2, 0.6+/−0.2; and 3.4+/−0.8 respectively) and colon shortening was less (10.3+/−0.5 centimeters). The improvements in percent weight loss (61 percent), DAI (53 percent) and colon shortening (29 percent) were statistically significant, p less than 0.05.

Simethicone produced improvements in all measures of colitis severity except weight loss. Compared to control, weight loss was nearly the same (25.7% (sem+/−4.1 percent), scores for diarrhea, bloody stool and DAI was less (1.0+/−0, 0.8+/−0.3 and 5.5+/−0.4 respectively) and colon shortening was less (8.6+/−0.3 centimeters). The greatest improvement was in the score for bloody stools; bleeding was reduced by 38 percent.

The combination of sulfasalazine and simethicone produced moderate to large improvement in all measures of colitis severity. Compared to respective control values, weight loss was less (13.6%; sem+/−2.3 percent), scores for diarrhea, bloody stools and DAI were less 0.9+/−0.1, 0.2+/−0.2, and 4.1+/−0.4, respectively) and colon shortening was less (colon length 9.6+/−0.2 centimeters). The improvements in percent weight loss (49%), bloody stools and colon shortening (20%) were statistically significant, p less than 0.05. The greatest improvement was in the score for bloody stools, bleeding was almost completely suppressed (83 percent), an effect much greater than that produced by either sulfasalazine or simethicone alone.

The above results indicate that simethicone at a low dosage of about 10 mg/kg is effective in the treatment of ulcerative colitis and the combination of sulfasalazine and simethicone is unexpectedly very effective.

We claim:

1. A method for treating ulcerative colitis comprising orally providing from about 1.0 to about 20 mg/kg of body mass of simethicone.

2. The method of claim 1 which additionally comprises an effective amount of sulfasalazine.

3. The method of claim 2 wherein the amount of sulfasalazine is from 0.5 mg/kg to about 80 mg/kg of body mass.

4. An orally administered composition useful for reducing the symptoms of ulcerative colitis comprising an effective amount of sulfasalazine to reduce the symptoms of ulcerative colitis and from about 1.0 to about 20 mg/kg of body mass of simethicone.

5. The oral composition of claim 4 wherein the sulfasalazine is from about 0.5 mg/kg to about 80 mg/kg of body mass.

6. The method of claim 1 that is administered daily.

7. The composition of claim 4 that is administered daily.

8. The composition of claim 5 that is administered daily.

9. A method for treating ulcerative colitis comprising orally providing from about 5.0 to about 10 mg/kg of body mass of simethicone.

10. The method of claim 9 which additionally comprises an effective amount of sulfasalazine.

11. The method of claim 10 wherein the amount of sulfasalazine is from 0.5 to about 80 mg/kg of body mass.

12. The oral composition of claim 4 wherein the amount of simethicone is from about 5 to about 10 mg/kg of body mass.

13. The oral composition of claim 12 wherein the sulfasalazine level is from about 0.5 to about 80 mg/kg of body mass.

* * * * *